United States Patent [19]
Daglow et al.

[11] Patent Number: 5,370,669
[45] Date of Patent: Dec. 6, 1994

[54] IMPLANTABLE CARDIAC DEFIBRILLATOR WITH LAYERED PACKAGE

[75] Inventors: Terry D. Daglow; Kenneth R. McNeil, II, both of Lake Jackson; Balakrishnan Shankar, Pearland, all of Tex.

[73] Assignee: Intermedics, Inc., Angleton, Tex.

[21] Appl. No.: 154,211

[22] Filed: Nov. 17, 1993

[51] Int. Cl.⁵ ............................................. A61N 1/375
[52] U.S. Cl. .................................................... 607/36
[58] Field of Search ..................... 607/36, 37, 4, 5, 6, 607/7, 8

[56] References Cited

U.S. PATENT DOCUMENTS

| | | |
|---|---|---|
| 4,254,775 | 3/1981 | Langer. |
| 5,103,818 | 4/1992 | Maston et al. ........................ 607/36 |
| 5,131,388 | 7/1992 | Pless et al. . |
| 5,282,841 | 2/1994 | Szyszkowski ........................ 607/37 |

*Primary Examiner*—William E. Kamm
*Assistant Examiner*—Scott M. Getzow
*Attorney, Agent, or Firm*—John R. Merkling

[57] ABSTRACT

An implantable medical device, and more particularly a fully implantable defibrillator which may also include bradycardia and cardioversion pacing, in which the components of the device are housed within an implantable casing having three orthogonal dimensions of height, width and thickness. The height and width are substantially greater than the thickness. The implantable device comprises three major sub-systems, specifically, the batteries, the power capacitors, and the electronics. Each of the three sub-systems lie in parallel height-width planes, each plane being adjacent another in the thickness dimension.

9 Claims, 2 Drawing Sheets

IMPLANTABLE CARDIAC DEFIBRILLATOR WITH LAYERED PACKAGE

BACKGROUND OF OUR INVENTION

Our invention relates to the packaging of implantable life assisting devices in general, and to the packaging of a fully implantable cardiac defibrillator in particular. Since the early work of Mieczyslaw Mirowski, substantial effort has been devoted to the development of fully automatic, implantable cardiac defibrillators. Most recently, these devices have been combined with bradycardia pacing and cardioversion pacing in addition to their defibrillating functionality. From the beginning, it has been recognized that such an implantable defibrillator should have a small size as an essential characteristic, particularly because it must be implanted within the patient's body. Efforts have also been made to isolate the defibrillator components from corrosive attack by biological fluids within the body and to isolate certain defibrillator components from the effects of other components, such as energy storage devices, should these components release gases or fluids. In particular, batteries and the requisite high voltage capacitors have presented challenges to the designers of defibrillator packages.

In general, the prior art has incorporated large cylindrical power capacitors into the packaging of the implantable defibrillator. A representative design is disclosed in U.S. Pat. No. 4,254,775. The packaging described in the '775 patent shows a implantable defibrillator having mutually orthogonal dimensions of height, width and thickness. The first two dimensions, height and width, are substantially larger than the remaining dimension, thickness. Tubular or cylindrical power capacitors are shown which extend substantially the entire thickness of the packaging. The diametrical dimension of power capacitors, therefore, have been a substantial limitation on the design of packaging for implantable defibrillators.

More recently, flat power capacitors have been proposed for use in defibrillators. For example, U.S. Pat. No. 5,131,388 proposes the manufacture of a flat electrolytic capacitor. The design shows a packaging having, once again, three orthogonal dimensions of height, width and thickness, with height and width being substantially larger than the thickness. As shown in the design in the '388 patent, the power capacitors and the electronic of the defibrillator lie in substantially the same plane defined by the height and width dimensions and have substantially the same thickness. In fact, the power capacitor partially surrounds the electronics on three sides.

Although progress has been made in packaging implantable defibrillators, there remains a need for improved packaging, particularly packaging which can rapidly accommodate changes in electronics, battery and power capacitor technologies. We believe that the design should accommodate changes in any one of these three principle components of a implantable defibrillator system without requiring corresponding alterations in another system. Our invention is directed towards these needs.

SUMMARY OF OUR INVENTION

Our invention relates to a fully implantable defibrillator which may also include bradycardia and cardioversion pacing, in which the components of the device are housed within an implantable casing having three orthogonal dimensions of height, width and thickness. The height and width are substantially greater than the thickness. The implantable device comprises three major sub-systems, specifically, the batteries, the power capacitors, and the electronics. In addition, an implantable defibrillator frequently comprises a power transformer and a communications coil. For purposes of this invention, the power transformer and communication coil are not considered to be part of the electronics. In our invention, each of the three sub-systems defined above lie in parallel height-width planes each plane being adjacent another in the thickness dimension. Because there is substantially no overlap in the thickness dimension between the three sub-systems, a change in technology effecting any of the three sub-systems can be accommodated by a change in the thickness of the overall device alone. Thus, the development of thinner power capacitors can be immediately incorporated into a change in the thickness dimension of the packaging of a implantable defibrillator, without requiring a change in design of the overall defibrillator or of the other components of the defibrillator. Similarly, changes in battery technology, or in the electronics packaging which result in a change in thickness of these sub-systems, can be accommodated simply by the alteration of one dimension of the overall packaging for the cardiac defibrillator.

Moreover, special needs of particular patients can be more easily met in a plurality of devices having the same overall configuration in height and width, but differing in thickness. Thus, a patient requiring and accommodating greater battery capacity could have a implantable defibrillator whose packaging was thicker, thus having additional thickness for larger batteries, while a patient needing a thin defibrillator could receive a device more adapted for his or her needs. Because changes in power capacitor thickness could be accommodated with only a change in dimension in the thickness of the packaging and not in other dimensions or in changes in electronics, such special requirements could more easily and inexpensively be met with our invention.

In view of the foregoing, it is an object of our invention to provide compact implantable defibrillator having a structure which accommodates varying thickness, while standardizing dimensions and design in height and width.

It is also an object of our invention to provide a package in design which can accommodate changes in technology in any of three sub-systems, specifically, batteries, power capacitors and electronics.

It is also a object of our invention to provide packaging which can be optimized to accommodate changes in the various sub-system technologies.

Another object of our invention is to provide a package for an implantable defibrillator which can accommodate custom capabilities.

These and other objects and features of our invention will be apparent from the following description taken with reference to the accompanying draws.

DETAILED DESCRIPTION OF OUR PREFERRED EMBODIMENT

We will now describe our preferred embodiment, in connection with the accompanying figures. In all the drawings, like numerals will be used to designate like parts.

Figure 1:
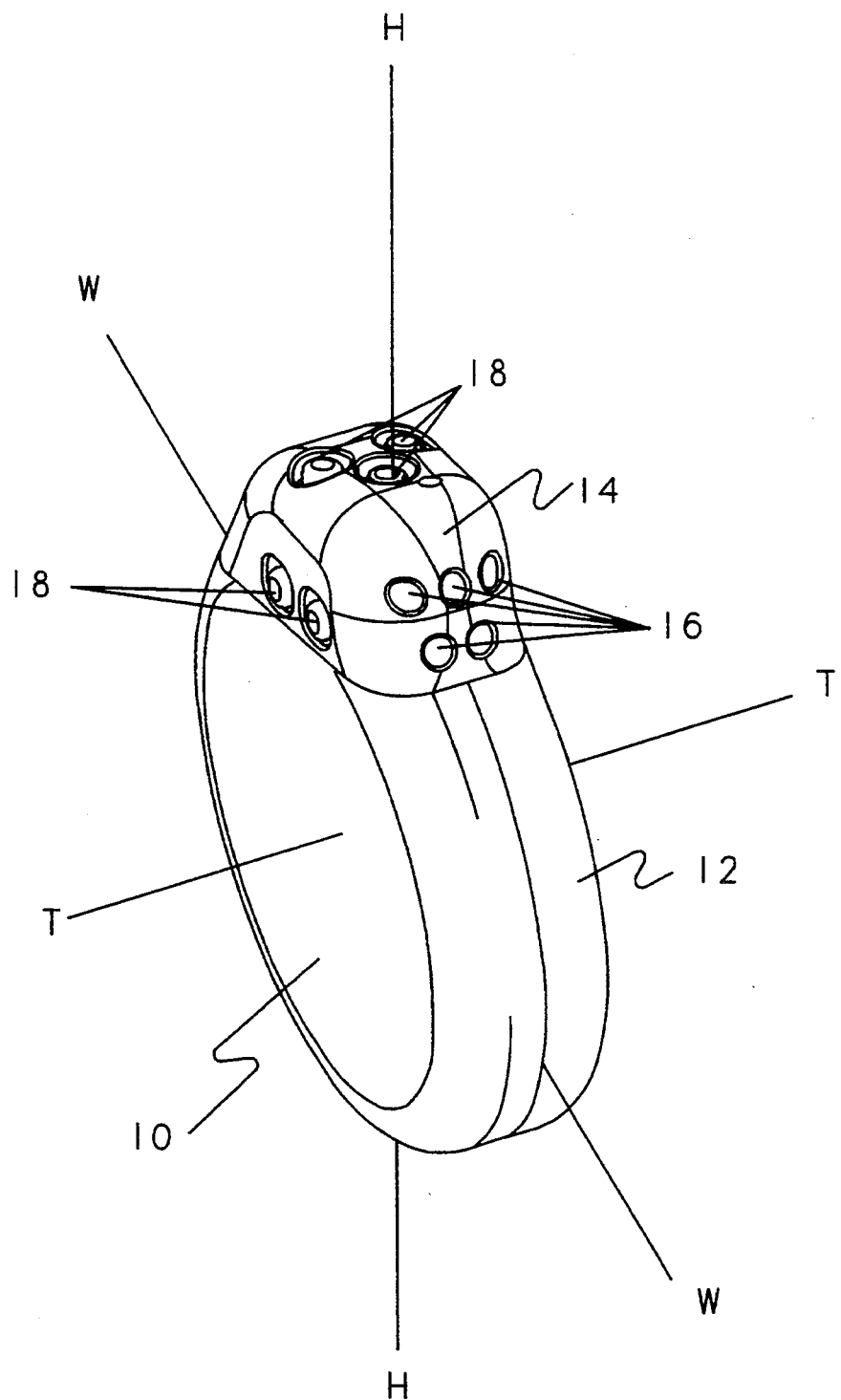
FIG. 1 is a perspective view of a cardiac defibrillator package according to our present invention.

FIG. 1 illustrates a perspective view of an implantable cardiac defibrillator 10 in a package according to our present invention. The defibrillator 10 comprises a case 12 of titanium alloy and a header 14 of epoxy. We define three mutually orthogonal dimensions of height, width and thickness. For purposes of this description, the height may be deemed to be the dimension passing through the header 14 and designated by the line H in FIG. 1. The width dimension is orthogonal thereto and designated by the line W in the figure. The thickness lies along the line T in the figure and designates the smallest of the three overall dimensions of the defibrillator. In our preferred embodiment, the defibrillator is bilaterally symmetrical around the HW plane.

The header 14 has a plurality of ports 16 for receiving distal ends of leads (not shown). In our illustrated embodiment, five ports 16 are shown. This would accommodate three high voltage electrodes, and pacing and sensing electrodes for the atrium and the ventricle. Associated with each port 16 is a set screw 18.

Figure 2:
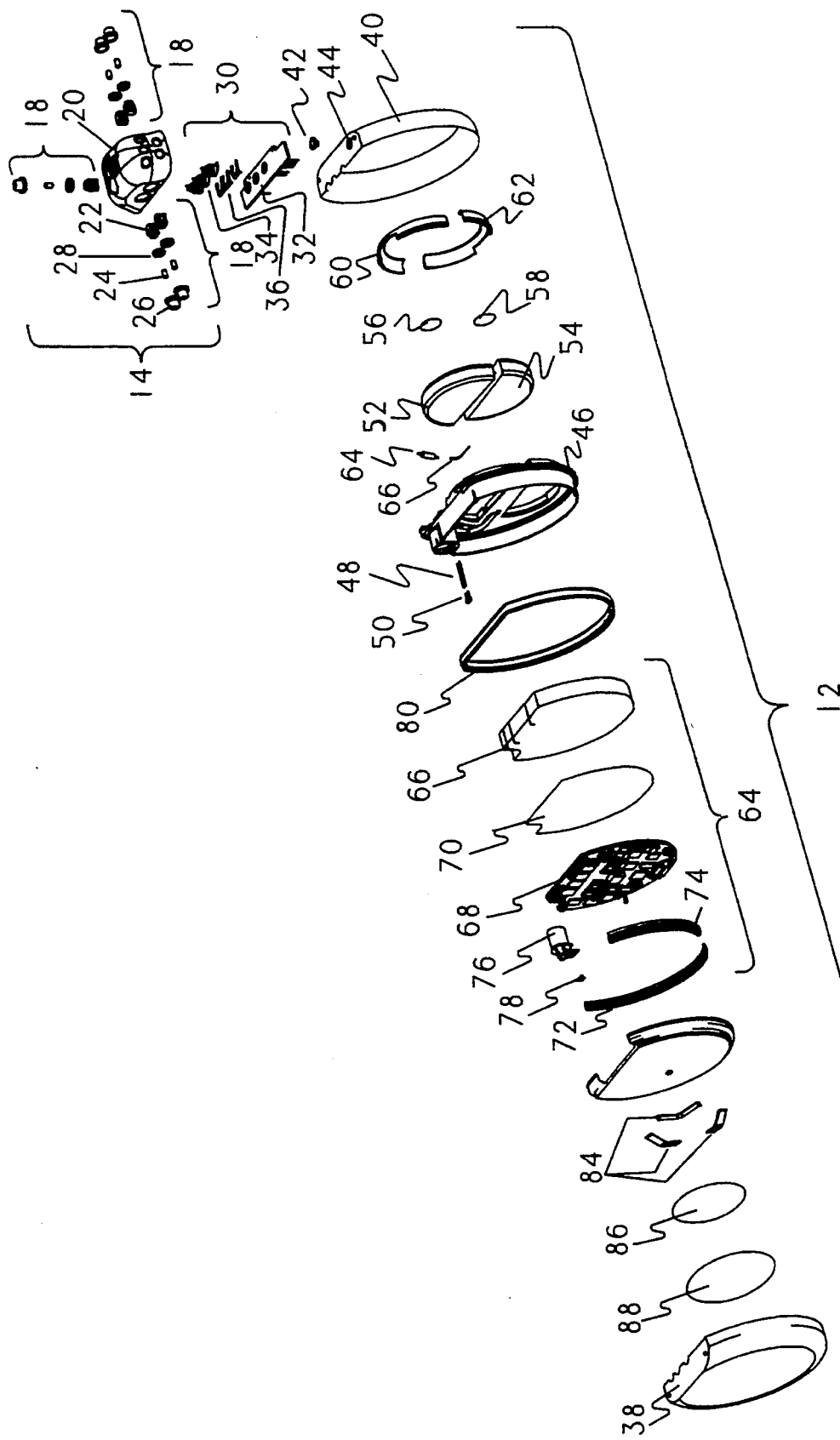
FIG. 2 is an exploded perspective view of the cardiac defibrillator packaging of FIG. 1.

We will now explain our invention in greater detail with reference to the exploded view shown in FIG. 2. The header 14 comprises an epoxy header body 20 which receives both the set screws 16 and the distal ends of the leads (not shown). Each set screw 18 comprises a set screw block 22 which couples the set screw with the distal end of the lead. A screw 24 is threadedly received into the screw block 22. A cap 26 drives the screw 24. Between the set screw block 22 and the cap 26, a seal 28 is provided to exclude body fluids from the interior of the header.

The header is electrically connected to the interior of the defibrillator assembly by a feed-through flex assembly 30. The flex assembly 30 comprises a flex connector 32 and a plurality of electrical connection posts 34 which are fastened by clips 36. An electrical connection through one or more posts must be provided for each channel of input or output desired.

The case 12 has front and back titanium shells, 38, 40 respectively, which mate together and which can be sealed as by welding. A purge plug 42 is provided in a purge hole 44 in one of the shells so that the case may be filled with nitrogen gas after assembly. We will now describe simultaneously the parts contained within the two shells, and our preferred method of assembly.

We have provided a polymeric retainer 46 to receive most of the components described hereafter. The retainer 46 has spaces to receive batteries, power capacitors, power transformers and other components necessary for the implantable defibrillator. We begin by inserting platinum wires 48 with attached post connectors 50 into a portion of the retainer which will receive a power transformer, to be described hereafter. Two lithium batteries 52, 54, such as lithium silver vanadium batteries available from Wilson Greatbatch Company, are prepared with insulator dots 56, 58 of polyamide and with external retaining clips 60, 62 of polypropylene. The dots and clips insulate the batteries from the shell 40. A fuse 64 and jumper wire 66 may also be provided. The assembly of the batteries with insulator dots and clips is then inserted into the retainer 46. The retainer 46 and the battery assembly are then laid as a unit into the back shell 40.

An electronics subassembly 64 is then assembled. The electronics subassembly 64 comprises the power capacitors 66 and an electronics hybrid 68 which supports substantially all of the electronics for the defibrillator. It will be noted that the power capacitor 66 has substantially the same outline in the height/width plane as the case 38, 40 itself. Both the batteries 52, 54 and the power capacitor 66 lie in separate, substantially parallel planes which are parallel to the height/width plane. The electronics hybrid 68 is also shaped similarly to the casing in the height/width plane and lies in its own plane, parallel to the planes of the batteries and of the power capacitor. The power capacitor and the electronics hybrid are separated by a polyamide spacer 70. Each of these components (the power capacitor 66, the electronic hybrid 68 and the spacer 70) are assembled in stacked relationship to one another using polypropylene edge clips 72, 74. The electronics subassembly 64 is then placed into the retainer 46 on a front side thereof. A power transformer 76 is then inserted into the retainer 46. The power transformer, as is known in the art, is used to step up the voltage of the batteries to a higher voltage for storage on the power capacitor 66. As shown in FIG. 2, the power transformer extends across the planes of the electronics and the power capacitor and, for purposes of our invention is not considered a part of the electronics sub-system, which is carried on the power hybrid 68. A jumper 78 is provided to connect the power transformer 76 to the hybrid 68. A communications coil 80, preferably prewound on a polyamide backing, can then be set around the retainer 46.

At this stage, the feedthrough flex assembly 30 is connected to the circuitry on the electronics hybrid 68, so that the defibrillator will be able to communicate through the can to the header when it has been assembled. A hybrid lid 82, preferably of stainless steel, is then placed over the exposed hybrid 68. On top of the hybrid lid, we have provided a buzzer assembly comprising a plurality of springs 84 and a stainless steel and piezoelectric sandwich sheet 86. It is know in this art to provide various signals including audio signals to alert the patient or physician to potential conditions, such as the eminent delivery of a defibrillating shock. The buzzer assembly is then covered with a polyamide spacer 88 and the front shell 38 of the can is fit over the assembly so that it mates back shell 40. The two shells are then laser welded together. We then fill the can with nitrogen gas through the purge hole 44 and insert the purge plug 42 to seal the can.

Finally, the header, described above, is assembled on the defibrillator in a known manner, by molding the epoxy header onto the can and assembling and inserting the set screws.

We claim as our invention:
1. An implantable medical device comprising
an external casing having mutually orthogonal dimensions of height, width and thickness;
electronics means for providing electrical therapy to the body of a patient, said electronics means lying substantially in a single electronics plane,
capacitor means for providing high-energy output, said capacitor means lying substantially in a single capacitor plane, and
battery means for providing an energy source, said battery means lying substantially in a single battery plane, said electronics, capacitor and battery planes being substantially parallel to each other and parallel to a plane defined by said height and width dimensions.

2. The implantable medical device according to claim 1 wherein said dimensions of height and width are substantially larger than said dimension of thickness.

3. The implantable medical device according to claim 2 further comprising a power transformer.

4. The implantable medical device according to claim 3 further comprising an antenna.

5. The implantable medical device according to claim 4 wherein said device comprises an automatic defibrillator.

6. The implantable medical device according to claim 1 further comprising a power transformer.

7. The implantable medical device according to claim 6 further comprising an antenna.

8. The implantable medical device according to claim 1 wherein said device comprises an automatic defibrillator.

9. The implantable medical device according to claim 8 wherein said dimensions of height and width are substantially larger than said dimension of thickness.

* * * * *